(12) United States Patent
Fisher et al.

(10) Patent No.: US 8,936,923 B2
(45) Date of Patent: Jan. 20, 2015

(54) PRODUCTION OF BIODIESEL

(75) Inventors: Lindsay Fisher, Mona Vale (AU); David Nicholls, Mona Vale (AU); Kevin Sanderson, Mona Vale (AU)

(73) Assignee: Biomass Research & Refining Pty Ltd, New South Wales (AU)

( * ) Notice: Subject to any disclaimer, the term of this patent is extended or adjusted under 35 U.S.C. 154(b) by 455 days.

(21) Appl. No.: 12/440,451

(22) PCT Filed: Dec. 5, 2007

(86) PCT No.: PCT/AU2007/001881
§ 371 (c)(1),
(2), (4) Date: Mar. 6, 2009

(87) PCT Pub. No.: WO2008/067605
PCT Pub. Date: Jun. 12, 2008

(65) Prior Publication Data
US 2010/0041112 A1    Feb. 18, 2010

(30) Foreign Application Priority Data

Dec. 5, 2006  (AU) ............................... 2006906788
May 10, 2007  (AU) ............................... 2007902481

(51) Int. Cl.
| C12P 7/64 | (2006.01) |
| C07C 51/43 | (2006.01) |
| C11B 3/00 | (2006.01) |
| C11B 7/00 | (2006.01) |
| C11B 13/00 | (2006.01) |
| C10L 1/18 | (2006.01) |
| C11C 3/00 | (2006.01) |
| C11B 1/00 | (2006.01) |
| C10L 1/02 | (2006.01) |

(52) U.S. Cl.
CPC . *C11C 3/003* (2013.01); *C11B 1/00* (2013.01); *C12P 7/649* (2013.01); *C10L 1/026* (2013.01); *Y02E 50/13* (2013.01); *C12P 7/6409* (2013.01); *C10G 2300/1011* (2013.01)
USPC .............................. 435/135; 554/174; 44/401

(58) Field of Classification Search
None
See application file for complete search history.

(56) References Cited

U.S. PATENT DOCUMENTS 6,451,567 B1  9/2002  Barclay
6,982,155 B1  1/2006  Fukuda et al.

OTHER PUBLICATIONS

Singh, A., Wilson, S., and Ward, O.P. (1996) Docosahexaenoic acid (DHA) production by *Thraustochytrium* sp. ATCC20892. World J. Microbiol. Biotech. 12, 76-81.*
Miao, X and Wu, Q. (2005) Biodiesel production from heterotrophic microalgal oil. Bioresource Technology 97; 841-846.*
Chang et al. (2011) Phytochemistry 72; 1460-1465.*
Tyson et al. (2004) Biomass Oil Analysis: Research Needs and Recommendations. National Renewable Energy Laboratory, NREL/TP-510-34796.*
Liang et al. (2010) Bioresource Technology 101: 7581-7586.*
Pinzi et al. (2009) Energy & Fuels, 23, 2325-2341.*
Liang et al. (2010) Bioresource Technology 101 pp. 7581-7586.*
Pinzi et al. (2009) Energy and Fuels 23, 2325-2341.*
Chang et al. (2011) Phytochemistry 72, 1460-1465.*
Chang et al. (2012) Appl. Microbiol. Biotechnol. 93: pp. 2215-2231.*
P.K. Bajpai et al: "Optimization of production docosahexaenoic acid (DHA) by *Thraustochytrium aureum* ATCC 34304", J Am Oil Chem Soc, vol. 68 (7), 1991, pp. 509-514.
R.D. Bowles et al: Long-chain n-3 polyunsaturated fatty acid production by members of the marine protisan group the thraustochytrids: screening of isolates and optimization of docosahexaeonic acid production:, Journal of Biotechnology, vol. 70, 1999 pp. 193-202.
A.M. Burja et al: Isolation and characterization of polyunsaturated fatty acid producing *Thraustochytrium* species: screening of strains and optimization of omega-3 production:, Apllied Microbiology and Biotechnology, vol. 72 (6), 2006, pp. 1161-1169.
J. Huang et al: "Grouping newly isolated Docosahexaenoic acid-producing Thrrasutochytrids based on their polyunsaturated fatty acid profiles and comparative analysis of 18S rRNA genes", Marine Biotechnology, vol. 5, 2003, pp. 450-457.
X. Miao et al: "Biodeisel production from heterotrophic microalgal oil" Bioresource Technology, vol. 97, 2006, pp. 841-846.
J. Sheehan et al: "A look back at the U.S. Department of Energy's aquatic species program: Biodiesel from Algae" [Online] Jul. 1998, National Renewable Energy Laboratory, U.S. Department of Energy, Golden, Colorado, U.S., XP002419237. Retrieved from the Internet: URL:http://www1.eere.energy.gov/biomass/pdfs/biodeies.
A. Singh et al: "Docosahexaenoic acid (DHA) production by *Thraustochytrium* sp. ATCC 20892", World Journal of Microbiology and Biotechnology, vol. 12, 1996, pp. 76-81.
J.D. Weete et al: "Lipids and ultrastructure of *Thraustochytrium* sp. ATCC 26185", Lipids, vol. 32 (8), 1997 pp. 839-845.
ACEM 0004 of Thomas E Lewis 2001 "Characterization and Application of Australia thraustrochytrids" (PhD), Morris Miller Library, University of Tasmania.
Anon et al. "From smokestack to gas tank: biofuels from waste gases." Focus on Catalysts, Dec. 2006, p. 7.
Bajpai et al. "Optimization of production of docosahexaenoic acid (DHA) by *Thraustrochytrium aureum* ATCC 34304". J Am Oil Chem. Soc, (1991), vol. 68, No. 7, pp. 50-514.
Bligh et al. "A rapid method for total lipid extraction and purification". Can J. Biochecm Physiol, (1959), vol. 37, pp. 911-917.
Christi "Biodiesel from microalgae". Biotechnology Advances (2007), vol. 25, pp. 294-306.

(Continued)

Primary Examiner — Chris R Tate
Assistant Examiner — Russell Fiebig
(74) Attorney, Agent, or Firm — Edward J. Baba; Bozicevic, Field & Francis LLP

(57) ABSTRACT

The invention relates to the production of biodiesel feedstock and biodiesel. A process for producing a biodiesel utilizing a thraustochytrid is provided.

7 Claims, No Drawings

(56) References Cited

OTHER PUBLICATIONS

Dionisi et al. "Stability of cyclopropane and conjugated linoleic acids during fatty acid quantification in lactic acid bacteria." Lipids, (1999), vol. 34, pp. 1107-1115.

Fan et al. "Zoospore Chemotaxis of Mangrove Thraustrochytrids from Hong Kong." Mycologia, (2002), vol. 94, pp. 569-578.

Fan et al. "Eicosapentaenoic and docosahexaenoic acids production by and okara-utilizing potential of thraustochtrids". Journal of Industrial Microbiology and Biotechnology, (2001), vol. 27, No. 4, pp. 199-202.

Huang et al. "Profile of polyunsaturated fatty acids produced by Thraustochytrium sp. KK17-3". Journal of the American Oil Chemists' Society, (2001), vol. 78, No. 6, pp. 605-610.

Kumon et al. "A new labyrunthulid isolate, which solely produces n-6 docosapentaenoic acid". Applied Microbiology Biotechnology, (2003), vol. 63, pp. 22-28.

Lewis et al. "The biotechnological potential of thraustochytrids". Marine Biotechnology, (1999), vol. 1, pp. 580-587.

Li et al. "Production of docosahexaenoic acid by *Thraustochytrium rosem*". Journal of Industrial Microbiology, (1994), vol. 13, pp. 238-141.

Metz et al. "Production of polyunsaturated fatty acids by polyketide synthases in both prokaryotes and eukaryotes". Science, (2001), vol. 293, pp. 290-293.

Miao et al. "Biodiesel production from heterotrophic microalgal oil". Bioresource Technology, (2006) vol. 97, pp. 841-846.

Nichols et al. "Variation of Branched-Chain Fatty Acids Marks the Normal Physiological Range for Growth in *Listeria Monocytogenes*". Appl. Environ Mcrobiol, (2002), vol. 68, pp. 2809-2813.

Palleroni "Chamber for Bacterial Chemotaxis Experiments". Appl. Environ Microbiol, (1976), vol. 32, pp. 729-730.

Pinto et al. "Biodiesel: An Overview". J. Braz. Chem. Soc., (2005) vol. 16, pp. 1313-1330.

Tyson et al. "Biomass Oil Analysis: Research Needs and Recommendations", Jun. 2004.

Xu et al. "High quality biodiesel production from a microalgae *Chlorella* prothothecoides by heterotrophic growth in fermenters". Journal of Biotechnology, (2006), vo. 126, pp. 499-507.

Yokochi et al. "Optimization of docosahehexaenoic acid production by *Schizochytrium limacimum* SR21". Applied Microbiology and Biotechnology, (1998) vol. 49, pp. 72-76.

European Patent Office Standard Search Report dated Jun. 5, 2007.

International Search Report dated Jan. 24, 2008.

Jul. 1998 (Aug. 1998), National Renewable Energy Laboratory, U.S. Department of Energy, Golden, Colorado, U.S., XP002419237 Internet URL: http://www1.eere.emergy.gov/biomass/pdfs/biodesell_from_algae.pdf.

* cited by examiner

PRODUCTION OF BIODIESEL

FIELD OF THE INVENTION

The invention relates to the production of biodiesel feedstock and biodiesel.

BACKGROUND OF THE INVENTION

Reserves of fossil diesel and petroleum distillates are running out. Biodiesel is an alternative fuel source. Biodiesels include alkyl esters. The alkyl esters may be produced by the transesterification of fatty acids contained in a biodiesel feedstock.

Biodiesel feedstocks can be obtained from animal, plant or algae sources. Animal sources include fats such as tallow, lard, and yellow grease. Currently it is not economically feasible to use animal sources as biodiesel feedstocks for biodiesel production on a commercial scale. In any case, the supply of animal sources cannot meet the current demand for biodiesel feedstock.

Plant sources include soybean, rapeseed and palm oil. They also include waste products such as may be obtained from the use of these oils, for example from food manufacturing and processing industries and from hospitality industry, including restaurants and the like. Ultimately the infrastructure and production costs for producing biodiesel from plant sources are far greater than the costs for producing diesel from fossil reserves or petroleum distillates.

Algae have also been investigated as a source of fatty acid for a biodiesel feedstock. However, the "Aquatic Species Program", a research program on the use of algae for production of biodiesel which was conducted by the US National Renewable Energy Laboratory from 1978 to 1996 found that commercial production would require an algal strain having a capacity for fast growth rate and high lipid content. Such strains were found to be either very difficult to isolate or very difficult to culture on a commercial scale to provide an acceptable yield of fatty acids.

SUMMARY OF THE INVENTION

In certain embodiments there is provided a process for producing a feedstock for providing biodiesel, the process including the step of utilizing a thraustochytrid to form unsaturated fatty acids, thereby producing a feedstock for providing a biodiesel.

In other embodiments there is provided a process for producing a biodiesel, the process including the steps of utilizing a thraustochytrid to form unsaturated fatty acids and transesterifying the unsaturated fatty acids to form alkyl esters from the unsaturated fatty acids, thereby producing a biodiesel.

In other embodiments there is provided a process for selecting a thraustochytrid for production of a biodiesel feedstock, the process including the step of determining that a thraustochytrid produces more monounsaturated fatty acids than polyunsaturated fatty acids.

In other embodiments there is provided a process for selecting a thraustochytrid for production of a biodiesel feedstock, the process including the step of determining that a thraustochytrid can be induced to produce more monounsaturated fatty acids than polyunsaturated fatty acids.

In still further embodiments there is provided a sample of thraustochytrids for producing a biodiesel feedstock. The sample is characterised in that it contains one or more of:
(i) thraustochytrids that produce more monounsaturated fatty acids than polyunsaturated fatty acids; or
(ii) thraustochytrids that can be induced to produce more monounsaturated fatty acids than polyunsaturated fatty acids.

In further embodiments there is provided a bioreactor for producing a feedstock for providing a biodiesel. The bioreactor includes a culture of thraustochytrids as described above.

In other embodiments there is provided a biodiesel feedstock or a biodiesel produced according to a process described above.

In other embodiments there is provided a process for producing a feedstock for providing biodiesel, the process including the following steps:
selecting a thraustochytrid for producing an oil having unsaturated fatty acids, the thraustochytrid being characterised in that no more than 50% of the unsaturated fatty acids in the oil produced by the thraustochytrid are polyunsaturated fatty acids; and
utilizing the selected thraustochytrid to produce the oil, thereby producing a feedstock for providing a biodiesel.

In one embodiment the thraustochytrid is characterised in that no more than 25%, preferably no more than 10%, of the unsaturated fatty acids in the oil produced by the thraustochytrid are polyunsaturated fatty acids.

DETAILED DESCRIPTION OF THE EMBODIMENTS

Thraustochytrids are common marine microheterotrophs that feed as saprobes or occasionally as parasites. Generally they may be characterised by the presence of a sagenogenetosome, an ectoplasmic net, a cell wall with noncellulosic scales, and a life cycle consisting of vegetative cells, zoosporangium and zoospores.

Although originally thought to be primitive fungi, thraustochytrids have more recently been assigned to the subclass Thraustochytridae (Chromista, Heterokonta), aligning them more closely with the heterokont algae (e.g., brown algae with diatoms). Molecular analysis of their 18S ribosomal RNA genes shows conclusively that thraustochytrids are deeply divergent from oomycetes and close to labyrinthulids.

Examples of thraustochytrid genera include Aplanochytriu, Labyrinthuloides, Japonochytrium, Schizochytrium, Thraustochytrium and Ulkenia. Among these, a number of species are recognised including A. kerguelense, A. stocchinoi, L. haliotidis, L. minuta, L. yorkensis, J. marinum, S. aggregatum, S. limacinum, S. mangrovei, S. minutum, T. aggregatum, T. aureum, T. kinnei, T. motivum, T. multirudimentale, T. pachydermum, T. striatum, T. visurgense, U. profunda, U. radiata, and U. visurgensis.

The primary commercial interest in thraustochytrids has been in relation to their ability to produce polyunsaturated fatty acids (herein "PUFA") such as fatty acids of the omega-6 ($\omega$6 or n-6) series (including arachidonic acid) and omega-3 ($\omega$3 or n-3) series (including eicospentaenoic acid and docosahexaenoic acid). PUFA are known to be essential for development of neural tissue and for decreasing the incidence of coronary heart disease, stroke and rheumatoid arthritis. Thus, the focus to date has been on the isolation and culture of PUFA-producing thraustochytrids with the objective of providing products for improving human and animal nutrition.

The thraustochytrid strains that produce relatively high amounts of PUFA (herein "PUFA$^{high}$ strains") produce unsaturated oil of which about 90% is PUFA. For obvious commercial reasons, PUFA$^{high}$ strains have been much more intensely characterised than strains that produce unsaturated oil of which about 10% is PUFA (herein "PUFA$^{low}$ strains"). Indeed there has been little or no characterisation of PUFA$^{low}$ strains.

The inventors have now recognised that PUFA$^{low}$ strains are particularly important as these strains tend to produce unsaturated oils of which about 90% is monounsaturated fatty acid (MUFA), including palmitoleic acid (C16:1), oleic acid (C18:1), eicosenoic acid acid (C20:1) and erucic acid (C22:1).

Further, it has been found that unlike other algae and like organisms, some PUFA$^{low}$ thraustochytrid strains tend to produce an abundance of a particular type of MUFA and very little other MUFA or PUFA.

The degree of saturation of fatty acid chains is highly relevant as to suitability for biodiesel production because saturation at least in part determines (i) the solidification temperature of biodiesel and (ii) the oxidative and thermal stability of biodiesel.

In more detail, solidification temperature is a function of the length of alkyl chains and the number of carbon double bonds (C=C) in a biodiesel. Biodiesel having shorter alkyl chains and fewer double bonds tend to have higher solidification temperatures than those having longer chain lengths and higher saturation. This means that the latter can be used at lower ambient temperatures without solidifying whereas the former are useful in a narrower range of temperatures, and not at lower temperatures.

On the other hand, biodiesel having a greater abundance of polyunsaturated oils tend to have a higher rate of oxidation and therefore less stability than those that do not. For example, the relative rate of oxidation of oleic (C18:1), linoleic (C18:2) and linolenic (C18:3) acid is 1:15:25.

Oxidation of biodiesel is generally undesirable as it results in the formation of products such as alcohols that reduce flash point and therefore fuel efficiency, aldehydes that cause rancidity, and short chain fatty acids that are corrosive to engine components. Anti-oxidants can be used, however this adds to production cost.

In summary of the above, it is clear that the presence and number of carbon double bonds is an important characteristic: saturated fatty acids typically have higher solidification temperatures and therefore cannot be used at lower temperatures, whereas fatty acids that are polyunsaturated are susceptible to thermal and oxidative instability. In this context, the inventors' finding that thraustochytrid strains that are PUFA$^{low}$ tend to produce unsaturated oils of which about 90% is MUFA oil is particularly important to the production of biodiesel.

A further advantage of the use of thraustochytrid strains is that they can be maintained by fermentative culture and typically do not require a light source, for instance for photosynthesis. These characteristics allow the use of continuous culture, for instance in a bioreactor, to produce the MUFA oil. As well, the amount of MUFA oil produced per weight of a thraustochytrid tends to be much greater than from MUFA sources presently commonly used in the art.

Thus, in certain embodiments there is provided a process for producing a feedstock for providing biodiesel, the process including the step of utilizing a thraustochytrid to form unsaturated fatty acids, thereby producing a feedstock for providing a biodiesel.

The process may include a further step of harvesting the unsaturated fatty acids in the form of an oil from the thraustochytrid. In a further step, the process may include fractionating the unsaturated oil to obtain a MUFA.

In other embodiments there is provided a process for producing a feedstock for providing a biodiesel. The process includes the following steps:
  providing a energy source that is fermentable by a thraustochytrid;
  adding a thraustochytrid to the energy source;
  utilizing the thraustochytrid to ferment the energy source to form unsaturated oil;
  optionally fractionating the unsaturated oil to obtain a monounsaturated oil, thereby producing the feedstock.

In a first step of the process, an energy source is provided. As known in the art, an "energy source" is generally organic matter, such as plant material, vegetation, or agricultural waste that can be used as a fuel or energy source.

In one embodiment, the energy source is selected for production of MUFA. In these embodiments, PUFA may also be produced.

In other embodiments, the energy source is selected for production of MUFA only. In these embodiments, the energy source may be selected to minimise PUFA production.

In certain embodiments, the energy source is selected to cause PUFA$^{high}$ strains to produce MUFA.

In other embodiments, the energy source is selected to maximise production of MUFA by PUFA$^{low}$ strains.

The second step of the process involves adding a thraustochytrid to the energy source. The thraustochytrid is typically one that is a PUFA$^{low}$ strain. One skilled in the art can distinguish a PUFA$^{low}$ strain from a PUFA$^{high}$ strain using the techniques described in the Examples.

In some embodiments, PUFA$^{high}$ strains may be used provided that the energy source that is provided and conditions for fermentation influence a decrease in production of PUFA, so that the PUFA$^{high}$ strain essentially adopts a PUFA$^{low}$ strain phenotype.

The thraustochytrid may be naturally occurring or a genetically engineered variant. Examples of naturally occurring thraustochytrid strains are as described herein. A genetically engineered variant is typically one that has been modified to maximise MUFA production. For example, it may be derived from a PUFA$^{high}$ strain that has been manipulated to be provided with a PUFA$^{low}$ strain phenotype. This could be achieved by deleting the polyketide synthase system of a PUFA$^{high}$ strain. Yet another alternative is to chemically modify a PUFA$^{high}$ strain to inhibit the polyketide synthase system. Certain antibiotics can be provided for this purpose.

In a third step the process involves utilizing the thraustochytrid to ferment the energy source to form unsaturated oil. Typically, the fermentation conditions are selected for production of MUFA. In certain embodiments, only MUFA is produced. However, in most embodiments, at least a residual amount of PUFA is produced. The conditions selected for fermentation may be for minimising PUFA production, or for causing PUFA$^{high}$ strains to produce MUFA. In other embodiments, the fermentation conditions are selected to maximise production of MUFA by PUFA$^{low}$ strains.

Typically the energy source may be fermented for a time period and at a temperature as described herein.

The fermentation process is typically performed in a bioreactor. One example of a suitable bioreactor is one in which the energy source is subject to continuous or periodic stirring. The bioreactor may be adapted for continuous culture.

The unsaturated oil is obtained from the fermentation culture by releasing the oil from the thraustochytrids. This process may require lysing the thraustochytrids and extracting lipids from them.

The process may involve a fourth step which includes fractionating the unsaturated oil to obtain a monounsaturated oil, thereby producing the feedstock. This step may be required where a significant proportion of lipids extracted from the thraustochytrids are PUFA. The fractionation of monounsaturated oils from polyunsaturated oils may be achieved by processes known in the art.

In further embodiments there is provided a feedstock produced by the above described process. The feedstock typically contains MUFA and very little, if any, PUFA. Examples of particularly preferred feedstocks are those that contain palmitoleic acid (C16:1), oleic acid (C18:1), eicosenoic acid acid (C20:1) and erucic acid (C22:1). Oleic acid is particularly preferred.

In further embodiments there is provided a bioreactor for producing a feedstock for providing a biodiesel. The bioreactor includes:
a culture of thraustochytrids; and
an energy source for fermentation by the thraustochytrids to produce a feedstock in the form of an unsaturated oil.

The thraustochytrids and energy source are as described above.

In other embodiments there is provided a process for producing a biodiesel, the process including the steps of utilizing a thraustochytrid to form unsaturated fatty acids and transesterifying the unsaturated fatty acids to form alkyl esters from the unsaturated fatty acids, thereby producing a biodiesel.

In other embodiments there is provided a process for producing a biodiesel. The process includes the following steps:
providing an energy source that is fermentable by a thraustochytrid;
adding a thraustochytrid to the energy source;
utilizing the thraustochytrid to ferment the energy source to form unsaturated oil;
optionally fractionating the unsaturated oil to obtain monounsaturated oil; and
forming alkyl esters from the unsaturated oils, to produce a biodiesel.

Having obtained the unsaturated oil, the biodiesel can be obtained by techniques known to the skilled addressee. The aim of these techniques is to cause a transesterification of the fatty acids to produce alkyl esters. Examples include using strong mineral acids, such as sulfuric acid or a sulfonated ion exchange resin, and methanol in counter current systems at 80° C. to 85° C. under mild pressures.

A further technique commonly used in the art is hydrogenation. Hydrogenation is also known in the art as 'hardening' of an oil. Essentially, a proportion of the unsaturated fatty acids in the oil are caused to combine with hydrogen under the influence of a catalyst to produce either less unsaturated fatty acids or saturated fatty acids. Further, the hydrogenation process can be made to be selective. This selectivity can be influenced by various factors, including temperature and pressure, of the hydrogenation reaction. In the case of PUFA, the selectivity of the hydrogenation arises from the presence of the methylene interrupted double bond.

The advantage of the hydrogenation process being selective in relation to biodiesel production hydrogenation is that is can be used to convert PUFA oil to MUFA oil, rather than converting MUFA to saturated fatty acids. For example, an oil that contains a mixture of C18:2, C18:1 and C18:0 fatty acids undergoes selective hydrogenation to convert substantially all C18:2 to C18:1 before any C18:1 is converted to C18:0. Thus, in certain embodiments an oil is produced where all original PUFA is converted by hydrogenation to MUFA, and the hydrogenation process does not add any further saturated fatty acid.

In certain embodiments the biodiesel produced by any of the above described embodiments should have a fatty acid methyl ester content, where the fatty acid methyl ester has 4 or more double bonds, of less than about 1% m/m (g per 100 g biodiesel). It may also have a content of linolenic acid methyl ester (an esterified PUFA) of less than 12% m/m (g per 100 g biodiesel).

In other embodiments there is provided a process for producing a biodiesel, the process including the steps of utilizing a thraustochytrid to form unsaturated fatty acids and transesterifying the unsaturated fatty acids to form alkyl esters from the unsaturated fatty acids, thereby producing a biodiesel. The embodiment includes the step of hydrogenating the fatty acids to form monounsaturated fatty acids from polyunsaturated fatty acids. This hydrogenation can be carried out before or after transesterification.

Thus, in other embodiments there is provided a process for producing a biodiesel. The process includes the following steps:
providing an energy source that is fermentable by a thraustochytrid;
adding a thraustochytrid to the energy source;
utilizing the thraustochytrid to ferment the energy source to form unsaturated oil;
optionally fractionating the unsaturated oil to obtain monounsaturated oil;
subjecting the unsaturated oil to a hydrogenation process to convert polyunsaturated oil to monounsaturated oil; and
forming alkyl esters from the unsaturated oils, to produce a biodiesel.

In further embodiments there is provided in a process for producing a biodiesel the step of utilizing a thraustochytrid to ferment an energy source to produce unsaturated oil that is useful as a feedstock for production of a biodiesel.

In further embodiments there is provided a biodiesel produced by the above described process.

In other embodiments there is provided a process for determining whether a thraustochytrid may be used to produce a feedstock for providing a biodiesel. The process includes the following steps:
obtaining a thraustochytrid;
determining whether:
(i) the thraustochytrid produces more MUFA than PUFA; or
(ii) the thraustochytrid can be induced to produce more MUFA than PUFA;
to determine whether the thraustochytrid may be used to produce a feedstock for providing a biodiesel.

The inventors have found that thraustochytrids that produce more MUFA than PUFA are generally PUFA$^{low}$ strains. One skilled in the art can distinguish a PUFA$^{low}$ strain from a PUFA$^{high}$ strain using the techniques described in the Examples.

In still further embodiments there is provided a culture of thraustochytrids for producing a biodiesel feedstock. The culture is characterised in that it contains either:
(i) a PUFA$^{low}$ strain; or
(ii) PUFA$^{high}$ strain that can be induced to make more MUFA than PUFA.

In one embodiment there is provided a thraustochytrid as deposited in accession no. V07/029468 at the National Measurement Institute (formerly AGAL) of 51-65 Clarke Street, South Melbourne, Victoria Australia 3205 on 15 Nov. 2007 by the Applicant.

In another embodiment there is provided a use of a thraustochytrid as described herein in a process for producing or biodiesel or biodiesel feedstock as described herein.

EXAMPLES

Example 1

Isolating & Identifying A PUFA$^{low}$ Strain

Thraustochytrids's are degraders of plant material in marine ecosystems. They may be isolated from decaying marine vegetation in estuarine waters.

Two general and one selective isolation method are used. Decaying plant material was rinsed twice in sterile 50% seawater and plated directly on selective media. Thraustochytrids were concentrated from water samples by aseptically filtering the sample through 0.2 µm filters. Filters were retained and placed onto selective media. To selectively isolate thraustochytrid zoospores, samples (water or water plus plant material) were placed in a sterile Palleroni device (Palleroni, N J, 'Chamber for Bacterial Chemotaxis Experiments' (1976) 32 *Appl Environ Microbiol* 729-730.) Sterile 50% seawater water was added in each compartment to a level 2 mm above the bottom of the connecting channel. Sterile 5 µl capillary (Drummond "Micro-caps", Drummond Scientific Co.) tubes filled with sterile chemo-attractant (e.g. glutamic acid, cellulose or pectin) in 50% seawater were immersed in the channels. After a further 2 h incubation at 20° C., the capillaries were removed, washed externally with a jet of sterile 50% seawater and the contents spread on the surface of the agar medium. Different genera of thraustochytrid have differing response to the attractant allowing some selectivity to the isolation (Fan, K W, Vrijmoed, L L P, and Jones, E B G, 'Zoospore Chemotaxis of Mangrove Thraustochytrids From Hong Kong' (2002) 94 Mycologia 569-578.).

Samples were plated onto glucose-yeast extract-seawater agar (0.5% glucose, 0.5% yeast extract (Oxoid), 50% artificial seawater (20 g/L sea salts; Sigma), 1.5% agar (Oxoid)) containing antibiotics to prevent bacterial growth (penicillin, streptomycin) and cultured at room temperature for up to 7 days. Characteristic colonies (nonmycelial, yeast-like) were subcultured to purity on the same media.

Cultures were grown in either liquid or solid glucose-yeast extract-seawater medium for 7 days at room temperature. Biomass was recovered from liquid cultures by centrifuging at 6000 g for 20 mins. Biomass from solid cultures was recovered by scraping the plates with cleaned glass microscope slides.

The phenotype of PUFA$^{low}$ strains is determined by analysis of fatty acid methyl esters according to Nichols, D S et al., 'Variation of Branched-Chain Fatty Acids Marks the Normal Physiological Range for Growth in Listeria Monocytogenes.' (2002) 68 Appl Environ Microbiol 2809-2813.

Samples were extracted by a direct transesterification procedure (Dionisi, F., P. A. Golay, M. Elli, and L. B. Fay. 1999. Stability of cyclopropane and conjugated linoleic acids during fatty acid quantification in lactic acid bacteria. Lipids 34:1107-1115.) and demonstrated to yield fatty acid profiles comparable to those obtained by the Bligh-Dyer solvent extraction method (Bligh, E. G., and W. J. Dyer. 1959. A rapid method for total lipid extraction and purification. Can. J. Biochem. Physiol. 37:911-917). Briefly, samples were added to screw-cap test tubes containing 3 mL of methanol-chloroform-hydrochloric acid (10:1:1, V/V/V). The tubes were heated at 80° C. for 1 h before they were cooled to room temperature. After addition of Milli-Q water (1 mL), the resultant fatty acid methyl esters were extracted three times with 1.5 mL of hexane-chloroform (4:1, V/V).

Fatty acid methyl esters were analyzed by using a Hewlett-Packard 5890 II gas chromatograph and 5970A mass selective detector equipped with a cross-linked methyl silicone (film thickness, 0.33 µm) fused-silica capillary column (length, 50 m; internal diameter, 0.22 mm). Fatty acid methyl esters from all samples were identified by comparing the component spectra to the spectra of known standards. The double bond positions and geometry in monounsaturated isomers of selected samples were determined by producing and analyzing dimethyl disulfide adducts.

Example 2

Examples of PUFA$^{low}$ Strains

ACEM 0004 of Thomas E Lewis 2001 "Characterisation and application of Australia thraustochytrids (PhD), Morris Miller Library, University of Tasmania and F3-1 and H1-14 of Huang et al. 2003 "Grouping newly isolated docosahexaenoic acid-producing thraustochytrids based on their polyunsaturated fatty acid profiles and comparative analysis of 18s rRNA genes" Mar. Biotechnol. 5: 450-457 are examples of PUFA$^{low}$ strains. Other thraustochytrid strains that are PUFA$^{low}$ may have about 91% nucleotide sequence identity with the 18s rRNA sequences of these strains.

Example 3

Producing Biodiesel Feedstock

Processes for culture of thraustochytrids are generally shown in U.S. Pat. No. 6,451,567.

Typically, to be viable economically, the thraustochytrid strain is one that produces about 30-60% of MUFA on a dry weight basis and less than 1-2% C18:2.

The strain may be grown in a medium containing glucose, cellulose and glycerol. The latter is a by-product of biodiesel production.

The strain is provided in a bio-reactor at a starting concentration of about $10^2$-$10^4$ cells/mL.

The fermentation conditions are generally aerobic as desaturase is oxygen dependant. Agitation with a propeller or turbine may be used to mix and aerate the culture. Oxygen levels may be between 30-60%. Such levels may be readily achievable with mixing and not require supplementation with gas mixtures.

Light is generally not important for culture. A temperature range of about 20-28° C. is generally provided.

The maximal concentration of the culture for a batch system generally ranges from about 0.8 to about 48 g/L.

The culture is monitored by assessing growth by measuring absorbance or by examining with a microscope. Lipid content can be estimated by staining with microscopy or spectroscopy.

Most batch cultivation is for 7-10 days. For continuous culture there is continuous harvesting. The rate of harvesting may be determined by the growth rate of the strain. Typically dilution rates are set empirically based on the growth rate or in a chemistat type culture at a level to maintain an easily measurable parameter (e.g. pH, nutrient level, oxygen).

Example 4

Producing Biodiesel

The source of fatty acids may be an oil feedstock produced by a thraustochytrid, an isolated unsaturated oil feedstock from a feedstock produced by a thraustochytrid, or a hydrogenated oil feedstock of a feedstock produced by a thraustochytrid. The oil feedstock may be mixed with methanol, hydrochloric acid and other miscible organic solvents as appropriate to form a single phase mixture. Heating of the mixture for a defined period at a defined temperature in excess of 80° C. has been determined experimentally to maximise product yield of fatty acid methyl ester. The fatty acid methyl ester is then extracted from the reaction mixture with an appropriate blend of organic solvents and solvent and removed by concentration to yield the biodiesel product.

Example 5

Hydrogenation of Unsaturated Oil Or Fatty Acid Esters To Produce Biodiesel

Hydrogenation may be achieved by passing a stream of hydrogen gas, generated by means known in the art, through the heated oil feedstock produced by a thraustochytrid, or a transesterified oil feedstock produced by a thraustochytrid, in which is suspended a finely powdered catalyst (typically a Pt or Ni related material). Modifications and variations of the process may be made, including to the catalyst, process parameters, and methods of recovery of the catalyst, to tailor selectivity and maximise yield of less polyunsaturated product. This hydrogenation process may be conducted either before or after transesterification.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A process for producing a biodiesel comprising the steps:
 (a) producing oil by providing suitable conditions for a thraustochytrid strain to produce said oil, wherein the oil comprises unsaturated fatty acids, and the unsaturated fatty acids comprise both monounsaturated and polyunsaturated fatty acids;
 (b) harvesting the oil produced in step (a);
 (c) transesterifying the unsaturated fatty acids in the oil to form alkyl esters from the unsaturated fatty acids, to produce the biodiesel,
 wherein the thraustochytrid strain produces more MUFA than PUFA and is as deposited in accession no. V07/029468.

2. The process according to claim 1 including the further step of:
 harvesting the oil formed by the thraustochytrid prior to the step of transesterifying the oil to form alkyl esters.

3. The process according to claim 1 including the further step of:
 fractionating the oil to obtain monounsaturated fatty acids before transesterifying the unsaturated fatty acids.

4. The process according to claim 1 wherein the oil produced by the thraustochytrid includes unsaturated fatty acids of which about 90% is monounsaturated fatty acids.

5. The process according to claim 1 wherein the oil produced by the thraustochytrid includes unsaturated fatty acids of which at least about 50% is monounsaturated fatty acids.

6. The process according to claim 1 wherein the oil produced by the thraustochytrid includes unsaturated fatty acids of which about 10% is polyunsaturated fatty acids.

7. The process according to claim 1 wherein the thraustochytrid produces less than about 2% C18:2 on a dry weight basis.

* * * * *